United States Patent [19]

Fujii et al.

[11] Patent Number: 4,496,584
[45] Date of Patent: Jan. 29, 1985

[54] AMIDINE DERIVATIVES WITH ANTI-COMPLEMENT ACTIVITY

[75] Inventors: Setsuro Fujii, Toyonaka; Takashi Yaegashi; Toyoo Nakayama, both of Funabashi; Shigeki Nunomura, Chiba; Yojiro Sakurai, Kamakura; Toshiyuki Okutome, Tokyo, all of Japan

[73] Assignee: Torii & Co. Ltd., Tokyo, Japan

[21] Appl. No.: 370,647

[22] Filed: Apr. 21, 1982

[30] Foreign Application Priority Data

Apr. 28, 1981 [JP] Japan ................................ 56-64943

[51] Int. Cl.$^3$ .................... C11C 3/04; C07C 69/035; A61K 31/27; A61K 31/23
[52] U.S. Cl. .................................. 514/510; 514/529; 514/546; 514/549; 514/551; 514/552; 260/404.5; 260/410.5; 260/1; 260/122; 260/123; 260/124; 260/125; 260/128; 260/138; 260/139; 260/163; 260/168; 260/169; 260/171; 260/173; 260/221; 260/251; 260/134
[58] Field of Search ...... 260/410.5, 404.56, 404.5 PA, 260/404.5 R; 560/1, 122, 123, 124, 125, 128, 138, 139, 168, 169, 221, 251, 173, 171, 163, 134; 424/311, 312, 314, 300, 305, 313

[56] References Cited

FOREIGN PATENT DOCUMENTS 48433 3/1982 European Pat. Off. ............... 560/34
89611 5/1972 German Democratic Rep. .
55-154952 12/1980 Japan .
56-110664 9/1981 Japan ................................ 560/34

OTHER PUBLICATIONS

Pharmazie, 32(12), (1977), pp. 761–763, Wagner et al. (I), "Synthetische Inhibitoren der Serinproteinasen".
Chemical Abstracts, vol. 90, No. 5, Abstract No. 38710c, (1979), p. 468, Wagner et al. (II).
Pharmazie, 34(9), (1979), pp. 554–556, Labes et al., "Free-Wilson-Arylyse der Hemmirkung Von 4-substituierten Benzamidinen gegenuber Thrombin, Plasminund Tryissin".

Primary Examiner—Thomas A. Waltz
Attorney, Agent, or Firm—Beveridge, DeGrandi & Kline

[57] ABSTRACT

Amidino compounds represented by the formula

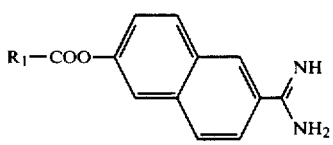

and pharmaceutically acceptable acid addition salts thereof are novel compounds and are useful as powerful antitrypsin, antiplasmin, antikallikrein and antithrombin agents. Having strong anti-Cl activity and anti-complement activity, they are also useful as anti-complement agents. These amidino compounds are prepared by reacting carboxylic compounds represented by the formula

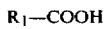

or their reactive intermediates with amidinonaphthol represented by the formula

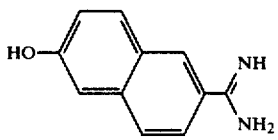

and, if necessary, can be transformed into pharmaceutically acceptable acid addition salts thereof.

2 Claims, No Drawings

AMIDINE DERIVATIVES WITH ANTI-COMPLEMENT ACTIVITY

This invention relates to amidine derivatives represented by the formula (I) or pharmaceutically acceptable acid addition salts thereof and to a process for the preparation thereof;

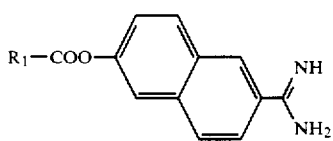
(I)

wherein $R_1$ represents a straight-chain or branched-chain alkyl group of 1 to 17 carbon atoms, a straight-chain or branched-chain alkenyl group of 2 to 6 carbon atoms having 1 to 3 double bonds, $R_2-(CH_2)_n-$, $R_3-(CH_2)_m-$, or

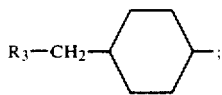

$R_2$ represents a cycloalkyl group of 3 to 6 carbon atoms or a cycloalkenyl group of 3 to 6 carbon atoms having 1 or 2 double bonds; n is 0, 1, 2 or 3; $R_3$ represents an amino or guanidino group or a protected amino or guanidino group; and m is an integer of 1 to 5.

An object of this invention is to provide a pharmaceutically useful compound.

The compound of the present invention is prepared by the reaction of a carboxylic acid represented by the formula (II)

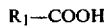
(II)

(wherein $R_1$ is as defined above) or a reactive intermediate thereof with amidinonaphthol of the formula (III)

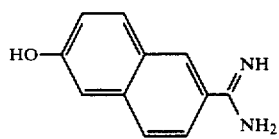
(III)

Still further, if desired, the present compound can be obtained by the removal of protective groups of amino and guanidino groups. The protective groups, as herein referred to, include those which are commonly used, such as, for example, benzyloxycarbonyl and tert-butoxycarbonyl groups.

For example, reduction of compounds having benzyloxycarbonylamino groups results in removal of the protective group and yields compounds having amino groups. The reactive intermediates, as herein referred to, include acid halides and acid anhydrides commonly used in the dehydration condensation and the reactive intermediates formed by reacting dicyclohexylcarbodiimide (DCC), diphenylphosphorylazide (DPPA), or the like with a carboxylic acid derivative.

Compounds of the present invention possess powerful inhibitory activities against trypsin, plasmin, kallikrein and thrombin, and are useful as anti-trypsin, anti-plasmin, anti-kallikrein and anti-thrombin agents. They possess also powerful anti-Cl-esterase activity and anti-complement activity and are useful as anti-complement agents.

In the above general formulas (I) and (II), the alkyl group is that having a straight or branched chain of 1 to 17 carbon atoms, such as, for example, methyl, ethyl, n-propyl, isopropy, n-butyl, isobutyl, tert-butyl, n-pentyl, n-hexyl, $C_9H_{19}$, $C_{11}H_{23}$, $C_{14}H_{29}$ and $C_{17}H_{35}$. The alkenyl group is that having a straight or branched chain of 2 to 6 carbon atoms with 1 to 3 double bonds such as, for example, ethenyl, propenyl, butenyl, 1,3-pentadienyl, and 2-methylpropenyl. The cycloalkyl group is that having 3 to 6 carbon atoms and the cycloalkenyl group is that having 3 to 6 carbon atoms with 1 or 2 double bonds. As examples, mention may be made of cyclopropyl, cyclobutyl, cyclopentyl, cyclopentenyl, cyclohexyl, cyclohexenyl, and cyclohexadienyl.

A process for producing the present compound is described below in detail by way of example.

The present compound (I) can be prepared by dissolving or suspending a carboxylic acid compound (II) in an organic solvent such as dimethylformamide, pyridine, or the like, then allowing the compound (II) to react with an ester activator such as dicyclohexylcarbodiimide (DCC), diphenylphosphoryl azide (DPPA), or the like, which is usually used as dehydration-condensation agent, and adding 6-amidino-2-naphthol (III) or preferably an acid addition salt thereof to the reaction product.

For instance, when DCC is used as the dehydration-condensation agent, a carboxylic acid derivative (II) is added to a solvent such as pyridine, then the mixture is stirred with cooling in ice or at room temperature for 10 minutes to 2 hours, then 6-amidino-2-naphthol (III) is added, and the mixture is further stirred at a temperature between $-30°$ and $80°$ C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding the filtrate to a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium bicarbonate solution to obtain the present compound (I) in the form of carbonate.

In the latter case, where the present compound remains dissolved in the reaction mixture, DCU is removed by filtration and the filtrate is admixed with a solvent such as ethyl ether, acetone, ethyl acetate, or the like to obtain the present compound (I).

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used are pharmaceutically acceptable ones sulfuric acid and phosphoric acid and organic acids such as acetic acid, lactic acid, citric acid, methanesulfonic acid, succinic acid, fumaric acid and maleic acid.

In another process, when it is intended to use an acid halide as a reactive intermediate of a carboxylic acid derivative (II), the latter derivative (II) is allowed to react with an acidhalogenation agent such as $SOCl_2$, $SOBr_2$, $PCl_5$ or the like to synthesize an acid halide represented by the formula (IV)

$$R_1COX \qquad (IV)$$

where $R_1$ is as defined above and X represents a halogen atom.

The acid halide is added to a solution of 6-amidino-2-naphthol (III), preferably in the form of an acid addition salt, dissolved in dimethylformamide, pyridine, dimethyl sulfoxide or the like and allowed to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of $-30°$ to $80°$ C., it is preferable for the purpose of avoiding side reactions to conduct the reaction in the early stage under ice cooling and then at room temperature. The reaction is complete in 2 to 5 hours, though the reaction mixture can be left overnight. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I). If desired, other acid addition salts can be prepared in a manner similar to that described above.

Anti-enzyme effect:

Compounds of the present invention possess powerful inhibitory activities against enzymes such as trypsin, plasmin, kallikrein and thrombin, and are effective as an anti-trypsin agent for the treatment of pancreatitis, as an anti-plasmin or anti-kallikrein agent for hemorrhagenic diseases, and as an anti-thrombin agent for thrombus.

The enzyme inhibitory activity was determined according to the method of Muramatsu et al. [M. Muramatsu, T. Onishi, S. Makino, Y. Hayashi and S. Fujii, J. Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylarginine methyl ester). The figure in parentheses shows the percentage inhibition at a concentration of the compound of $1 \times 10^{-5}M$.

The compound No. in Table 1 corresponds to that shown in Examples.

TABLE 1

| Compound No. | Trypsin | Plasmin | Kallikrein | Thrombin |
|---|---|---|---|---|
| 1 | $8 \times 10^{-5}$ | $2 \times 10^{-4}$ | $5 \times 10^{-4}$ | $4 \times 10^{-4}$ |
| 2 | $2 \times 10^{-5}$ | $3 \times 10^{-5}$ | $7 \times 10^{-4}$ | $2 \times 10^{-5}$ |
| 3 | $3 \times 10^{-5}$ | $3 \times 10^{-5}$ | $5 \times 10^{-4}$ | $8 \times 10^{-5}$ |
| 4 | $2 \times 10^{-5}$ | $2 \times 10^{-5}$ | $3 \times 10^{-4}$ | $3 \times 10^{-3}$ |
| 5 | $6 \times 10^{-6}$ | $1 \times 10^{-5}$ | $1 \times 10^{-4}$ | (26) |
| 10 | $2 \times 10^{-6}$ | $4 \times 10^{-6}$ | $1 \times 10^{-4}$ | $3 \times 10^{-6}$ |
| 12 | $2 \times 10^{-5}$ | $1 \times 10^{-5}$ | $>10^{-5}$ | $4 \times 10^{-5}$ |
| 15 | $1 \times 10^{-5}$ | (19) | $>10^{-5}$ | $>10^{-5}$ |
| 16 | $1 \times 10^{-5}$ | $3 \times 10^{-6}$ | $4 \times 10^{-5}$ | $1 \times 10^{-4}$ |
| 17 | $2 \times 10^{-4}$ | $4 \times 10^{-5}$ | $5 \times 10^{-5}$ | $6 \times 10^{-4}$ |
| 18 | $1 \times 10^{-5}$ | $3 \times 10^{-5}$ | $>10^{-5}$ | $4 \times 10^{-5}$ |
| 19 | $1 \times 10^{-6}$ | $8 \times 10^{-7}$ | $6 \times 10^{-6}$ | $3 \times 10^{-5}$ |
| 20 | (28) | $>10^{-5}$ | (38) | $>10^{-5}$ |

Anti-complement activity

The present compound and its pharmaceutically acceptable acid addition salts possess a strong $C1$ esterase ($\overline{C1r}$, $\overline{C1s}$) inhibitory activity, an ability of inhibiting the complement mediated hemolysis, and a therapeutic activity against the Forssman shock in which the activation of the complement system caused by an immune complex is said to play an important role. This indicates that the present compound is useful as an anti-complement agent effective for the treatment of allergic diseases such as nephritis associated with the complement. The test methods and test results are as shown below.

(1) In vitro test (anti-C1 esterase activity and inhibition of complement mediated hemolysis)

The anti-C1 esterase ($\overline{C1r}$, $\overline{C1s}$) activity was determined according to the method of Okamura et al. [K. Okamura, M. Muramatsu and S. Fujii, Biochem. Biophys. Acta, 295, 252-257 (1973)]. The inhibition of complement mediated hemolysis (percent) was determined according to the method of Baker et al. [B. R. Baker and E. H. Erickson, J. Med. Chem., 12, 408-414 (1969)]. The results obtained were as shown in Table 2. The figures in Table 2 have the following meanings:

$\overline{C1r}$: Molar concentration of the test compound which inhibits 50% of the ability of $\overline{C1r}$ to hydrolyse AAME (acetylarginin methyl ester) ($ID_{50}$).

$\overline{C1s}$: Molar concentration of the test compound which inhibits 50% of the ability of $\overline{C1s}$ to hydrolyse ATEE (acetyltyrosin ethyl ester) ($ID_{50}$).

Inhibition of complement mediated hemolysis (%): The inhibitory activity is shown in terms of percent inhibition of the compound at varied concentrations.

Compound No.: The compound number shown in Examples

TABLE 2

| Compound No. | Anti-$C_1$ activity | | Inhibition of complement mediated hemolysis (%) | | | |
|---|---|---|---|---|---|---|
| | $\overline{C1r}$ | $\overline{C1s}$ | $1 \times 10^{-4}$ | $1 \times 10^{-5}$ | $1 \times 10^{-6}$ | $1 \times 10^{-7}$ |
| 1 | $1 \times 10^{-5}$ | $2 \times 10^{-5}$ | 86 | 15 | 0 | 0 |
| 2 | $9 \times 10^{-6}$ | $2 \times 10^{-5}$ | 96 | 40 | 1 | 0 |
| 3 | $2 \times 10^{-6}$ | $2 \times 10^{-6}$ | 95 | 37 | 0 | 0 |
| 4 | $5 \times 10^{-6}$ | $4 \times 10^{-6}$ | 83 | 12 | 5 | 0 |
| 6 | | | 13 | 13 | 27 | 15 |
| 9 | | | 94 | 89 | 37 | 14 |
| 10 | $2 \times 10^{-7}$ | $3 \times 10^{-7}$ | 100 | 92 | 18 | 0 |
| 12 | $2 \times 10^{-6}$ | $3 \times 10^{-6}$ | 45 | 10 | 11 | 0 |
| 13 | | | 39 | 21 | 10 | 10 |
| 16 | $4 \times 10^{-6}$ | $4 \times 10^{-6}$ | 92 | 15 | 0 | 0 |
| 18 | $7 \times 10^{-5}$ | $9 \times 10^{-6}$ | 92 | 30 | 3 | 0 |
| 19 | $4 \times 10^{-7}$ | $4 \times 10^{-7}$ | 55 | 88 | 25 | 6 |

TABLE 2-continued

| Compound No. | Anti-C$_1$ activity | | Inhibition of complement mediated hemolysis (%) | | | |
|---|---|---|---|---|---|---|
| | C1r̄ | C1s̄ | 1 × 10$^{-4}$ | 1 × 10$^{-5}$ | 1 × 10$^{-6}$ | 1 × 10$^{-7}$ |
| 20 | 5 × 10$^{-6}$ | 4 × 10$^{-6}$ | 100 | 99 | 80 | 12 |

(2) Forssman shock

The experiment was performed according to the method of I. G. Offerness et al. [Biochem. Pharmacol., 27 (14), 1873-1878 (1978)]. Male Hartlay guinea pig of about 300 g in body weight was used. Each guinea pig of the control group was administered intravenously with 0.5 ml (minimum dose to cause the shock) of hemolysin (commercial hemolysin, 5,000 U as assayed by the method of Ogata) and the time elapsed until death was observed. For the test group, each guinea pig was administered intravenously with the test compound 5 minutes before the administration of hemolysin and the time (second) elapsed until death was observed. The results obtained were as shown in Table 3. As compared with the control group, the administered group showed a significant extension of survival time.

TABLE 3

| | Control group (sec.) | Group administered with Compound No. 20 (sec.) | |
|---|---|---|---|
| | | 1.0 mg/kg | 3.0 mg/kg |
| 1 | 530 | 360 | Survival |
| 2 | 390 | 365 | " |
| 3 | 245 | 325 | " |
| 4 | 425 | 620 | " |
| 5 | 445 | 650 | " |
| 6 | 530 | 325 | " |
| Average | 428 | 442 | |

Method of administration

The present compound is most suitably administered orally, though can be administered by injection for example. It is used as a drug either alone or in combination with other drugs. It is administered generally in the form of medicinal composition, though can be administered as simple substance without any additive. Examples of medicinal compositions include tablets, powders, capsules, syrups and solutions. An oral composition may contain common additives such as binders, excipients, lubricants, disintegrators and wetting agents. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifiers. For injection, aqueous suspensions or oily suspensions may be used.

Dosage

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of the illness.

Examples of pharmaceutical formulations are described below.

Examples of pharmaceutical formulations

| (1) Capsules. | | |
|---|---|---|
| The present compound | 100.0 | mg |
| Lactose | 59.0 | |
| Crystalline cellulose | 33.4 | |
| Calcium carboxymethylcellulose | 3.6 | |
| Magnesium stearate | 4.0 | |
| Total | 200.0 | mg |
| (2) Fine granules. | | |
| The present compound | 50.0 | mg |
| Lactose | 249.0 | |
| Mannitol | 75.0 | |
| Corn starch | 110.0 | |
| Hydroxypropylcellulose | 16.0 | |
| Total | 500.0 | mg |
| (3) Injections. | | |
| The present compound | 5.0 | mg |
| Distilled water for injection | 2 | ml |

Made up to injections in a customary manner.

Toxicity

The lethal dose (LD$_{50}$) of the present compound is as shown in Table 4.

TABLE 4

| | LD$_{50}$ Mouse (mg/kg) | |
|---|---|---|
| Compound No. | IP | PO |
| 1 | 200 | 2500 |
| 2 | 200 | 2500 |
| 20 | 175 | 2000 |

EXAMPLE 1

Synthesis of 6-amidino-2-naphthyl acetate (Compound No. 1)

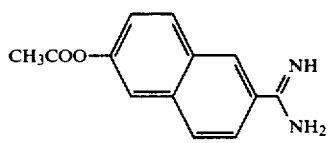

To 50 ml of anhydrous pyridine, was added 5.0 g of 6-amidino-2-naphthol methanesulfonate. To the mixture, while being stirred and cooled in ice, was added slowly dropwise 1.4 g of acetyl chloride. The mixture was stirred for 3 hours at room temperature and poured into stirred ethyl ether. The crystals were collected by filtration, washed with ethyl ether, dissolved in water, and poured into saturated aqueous sodium bicarbonate solution. The precipitated crystals were collected by filtration, washed with water, then with acetone, and dried to obtain 2.3 g of the carbonate of captioned compound. The salt was suspended in 20 ml of methanol. To the suspension, while being cooled in ice, was added 1.3 equivalents of methanesulfonic acid followed by ethyl ether to yield 1.7 g of white to pale brown crystals of 6-amidino-2-naphthyl acetate methanesulfonate.

Melting point: ca. 204° C.

IR $\nu_{max}^{KBr}$ cm$^{-1}$: 3275, 3080, 1760, 1670.

NMR (DMSO-d$_6$) δ: 2.35 (3H, s), 2.43 (3H, s), 7.33-8.63 (6H, m), 8.87-9.67 (4H, br).

EXAMPLE 2

Synthesis of 6-amidino-2-naphthyl n-butyrate (Compound No. 2)

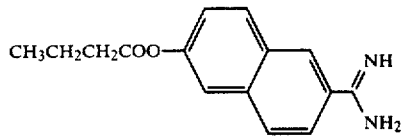

To a solution of 1.6 g of n-butyric acid in 50 ml of anhydrous pyridine, while being cooled in ice, was added 4.4 g of DCC. After stirring for 30 minutes, 5.0 g of 6-amidino-2-naphthol methane-sulfonate was added to the mixture and further stirred overnight at room temperature. The precipitate was collected by filtration, washed successively with a small volume of pyridine, ethyl ether, and acetone, and dissolved in methanol at room temperature. The insolubles were collected by filtration and washed with a small volume of methanol. The filtrate and the washings were concentrated under reduced pressure and admixed with ethyl ether. The precipitated crystals were recrystallized from ethanol to obtain 1.8 g of colorless flaky crystals of 6-amidino-2-naphthyl butyrate methanesulfonate.

Melting point: 238°–241° C.

IR $\nu_{max}^{KBr}$ cm$^{-1}$: 3300, 3100, 1750, 1670

NMR (DMSO-d$_6$) δ: 1.03 (3H, t), 1.75 (2H, m), 2.47 (3H, s), 2.67 (2H, t), 7.33–8.57 (6H, m), 9.07–9.63 (4H, br).

EXAMPLE 3

Synthesis of 6-amidino-2-naphthyl isovalerate (Compound No. 3)

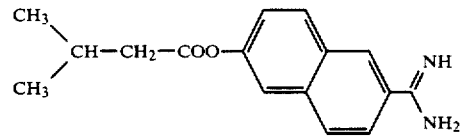

To a solution of 1.8 g of isovaleric acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was collected by filtration, washed with a small volume of pyridine, then with acetone, and dissolved in methanol at room temperature. The insolubles were collected by filtration and washed with a small volume of methanol. The filtrate and the washings were concentrated under reduced pressure and admixed with ethyl ether. The precipitated crystals were recrystallized from an ethanol-methanol (9:1) mixture to yield 2.0 g of colorless flaky crystals of 6-amidino-2-naphthyl isovalerate methanesulfonate.

Melting point: 250°–251.5° C.

IR $\nu_{max}^{KBr}$ cm$^{-1}$: 3300, 3120, 1750, 1675.

NMR (DMSO-d$_6$) δ: 1.07 (6H, d), 1.53–2.73 (3H, br), 2.47 (3H, s), 7.33–8.57 (6H, m), 9.00–9.60 (4H, br).

EXAMPLE 4

Synthesis of 6-amidino-2-naphthyl caproate (compound No. 4)

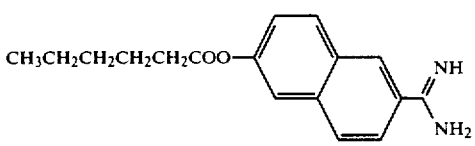

To a solution of 2.1 g of caproic acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate formed upon addition of ethyl ether to the reaction mixture was collected by filtration, washed with ethyl ether, dissolved in methanol at room temperature, and filtered to remove the insolubles. The filtrate was concentrated under reduced pressure and the residue was recrystallized from an ethanol-ether mixture to obtain 2.1 g of 6-amidino-2-naphthyl caproate methanesulfonate.

Melting point: 178°–180° C.

IR $\nu_{max}^{KBr}$ cm$^{-1}$: 3250, 3080, 1750, 1660.

NMR (DMSO-d$_6$) δ: 0.93 (3H, m), 1.50 (6H, m), 2.13 (3H, s), 2.67 (2H, m), 7.33–8.57 (6H, m), 9.10–9.60 (4H, br).

EXAMPLE 5

Synthesis of 6-amidino-2-naphthyl caprate (Compound No. 5).

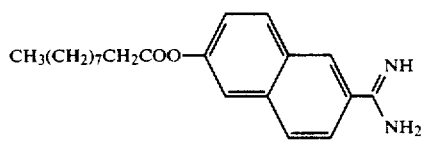

To a solution of 3.0 g of capric acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was separated by filtration and washed with a small volume of pyridine. The filtrate and washings were poured into stirred ethyl ether. The precipitated crystals were collected by filtration, washed with ethyl ether, then with acetone, and recrystallized from a methanol-ether mixture to yield 1.2 g of a white powder of 6-amidino-2-naphthyl caprate methanesulfonate.

Melting point: 165°–168° C.

IR $\nu_{max}^{KBr}$ cm$^{-1}$: 3300, 3130, 2900, 1750, 1680.

NMR (DMSO-d$_6$) δ: 0.87 (3H, m), 1.32 (14H, br-s), 2.45 (3H, s), 2.68 (2H, m), 7.35–8.68 (6H, m), 9.38 (4H, br).

EXAMPLE 6

Synthesis of 6-amidino-2-naphthyl laurate (Compound No. 6)

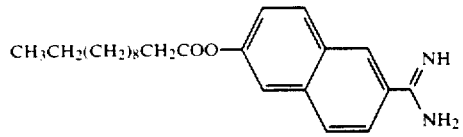

To a solution of 3.6 g of lauric acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was collected by filtration, washed with ether, then with acetone, dissolved in methanol, freed from the insolubles by filtration, concentrated under reduced pressure, and recrystallized from ethanol to yield 1.2 g of white crystals of 6-amidino-2-naphthyl laurate methanesulfonate.

Melting point: 149°–151° C.

IR $\nu_{max}^{KBr}$ cm$^{-1}$: 3300, 3125, 2900, 2840, 1750, 1670.

NMR (DMSO-d$_6$) δ: 0.68–1.95 (21H, br), 2.45 (3H, s), 2.62–2.85 (2H, br), 7.38–8.63 (6H, m), 9.10–9.60 (4H, br).

EXAMPLE 7

Synthesis of 6-amidino-2-naphthyl pentadecanoate (Compound No. 7).

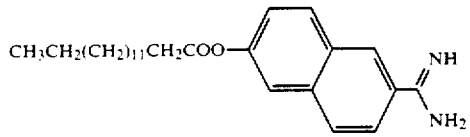

To a solution of 4.3 g of n-pentadecanoic acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was collected by filtration, washed with ethyl ether, then with acetone, dissolved in a methanol-dimethylformamide mixture, freed from the insolubles by filtration, and concentrated under reduced pressure. The crystals formed upon addition of ethyl ether were recrystallized from methanol to obtain 3.0 g of a white powder of 6-amidino-2-naphthyl pentadecanoate methanesulfonate.

Melting point: ca. 153° C.

IR $\nu_{max}^{KBr}$ cm$^{-1}$: 3300, 3100, 2900, 2840, 1745, 1660.

NMR (DMSO-d$_6$) δ: 0.65–1.92 (27H, br), 2.43 (3H, s), 2.58–2.85 (2H, br) 7.38–8.68 (6H, m), 9.15–9.65 (4H, br).

EXAMPLE 8

Synthesis of 6-amidino-2-naphthyl stearate (Compound No. 8)

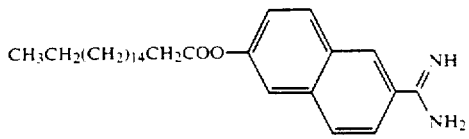

To a solution of 5.0 g of stearic acid in 70 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was collected by filtration, washed successively with a small volume of pyridine, ethyl ether, and acetone, dissolved in a dimethylformamide-methanol mixture, and filtered to remove the insolubles. The crystals formed upon addition of ethyl ether to the filtrate were collected by filtration, washed with ethanol, and recrystallized from a dimethylformamide-methanol mixture to obtain 3.3 g of a white to pale brown powder of 6-amidino-2-naphthyl stearate methanesulfonate.

Melting point: ca. 128° C.

IR $\nu_{max}^{KBr}$ cm$^{-1}$: 3300, 3120, 2900, 2850, 1750, 1670.

EXAMPLE 9

Synthesis of 6-amidino-2-naphthyl sorbate (Compound No. 9)

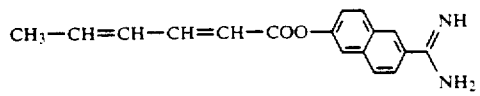

To a solution of 2.0 g of sorbic acid in 50 ml of anhydrous pyridine, while being cooled in ice, was added 4.4 g of DCC. After stirring for 30 minutes, 5.0 g of 6-amidino-2-naphthol methanesulfonate was added to the mixture and further stirred overnight at room temperature. The precipitate was collected by filtration, washed with ethyl ether, then with acetone, dissolved in methanol, and filtered to remove the insolubles. The filtrate was concentrated under reduced pressure and recrystallized from an ethanol-methanol mixture to yeild 2.4 g of colorless granular crystals 6-amidino-2-naphthyl sorbate methanesulfonate.

Melting point: 206°–209° C.

IR $\nu_{max}^{KBr}$ cm$^{-1}$: 3300, 3080, 1730, 1675

NMR (DMSO-d$_6$) δ: 1.87 (3H, br-d), 2.53 (3H, s), 6.05–6.60 (3H, m), 7.27–8.73 (7H, m), 9.10–9.73 (4H, br).

EXAMPLE 10

Synthesis of 6-amidino-2-naphthyl cyclopropanecarboxylate (Compound No. 10)

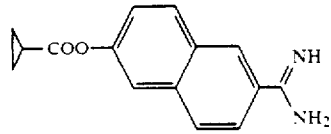

To a solution of 5.0 g of 6-amidino-2-naphthol methanesulfonate in 50 ml of anhydrous pyridine, while being cooled in ice, was added dropwise with stirring 1.9 g of cyclopropanecarbonyl chloride. The mixture was stirred overnight at room temperature, and the insolubles were separated and washed with a small volume of pyridine. The filtrate and the washings were poured into stirred ethyl ether. The crystals were collected by filtration, washed with ethyl ether, dissolved in water, and poured into stirred saturated aqueous sodium bicarbonate solution. The precipitated crystals were collected by filtration, washed with water, then with acetone, and dried to obtain 3.4 g of the carbonate of the captioned compound. To a suspension of the salt in 20 ml of methanol, while being cooled in ice, was added 1.2 equivalents of methanesulfonic acid followed by ethyl ether to obtain 3.0 g of white granular crystals of 6-amidino-2-naphthyl cyclopropanecarboxylate methanesulfonate.

Melting point: 214°–217° C.

IR $\nu_{max}^{KBr}$ cm$^{-1}$: 3270, 3120, 1745, 1675

NMR (DMSO-d$_6$) δ: 1.13 (4H, m), 2.02 (1H, m), 2.45 (3H, s), 7.37–8.57 (6H, m), 9.33 (4H, br).

EXAMPLE 11

Synthesis of 6-amidino-2-naphthyl cyclobutanecarboxylate (Compound No. 11)

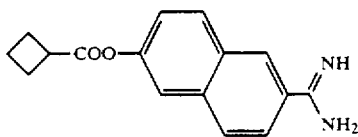

To a solution of 1.8 g of cyclobutanecarboxylic acid in 50 ml of anhydrous pyridine, while being cooled in ice and stirred, was added 4.4 g of DCC. After 30 minutes, 5.0 g of 6-amidino-2-naphthol methanesulfonate was added to the mixture and the mixture was further stirred for 24 hours at room temperature. The precipitate formed on addition of ethyl ether was collected by filtration, dissolved in dimethylformamide, and filtered to remove the insolubles. Ethyl ether was added to the filtrate and the precipitate which was formed was collected by filtration and recrystallized from a dimethylformamide-ethyl ether mixture to yield 3.3 g of a white powder of 6-amidino-2-naphthyl cyclobutanecarboxylate methanesulfonate.

Melting point: 225°–230° C.

IR $\nu_{max}^{KBr}$ cm$^{-1}$: 3400–3000, 1750, 1675, 1200, 1180, 1130, 1050, 780, 545, 520.

NMR (DMSO-d$_6$) δ: 2.53 (3H, s), 1.73–2.83 (6H, m), 3.17–3.67 (1H, m), 7.27–8.82 (6H, m), 9.07–9.83 (4H, br).

EXAMPLE 12

Synthesis of 6-amidino-2-naphthylcyclohexanecarboxylate (Compound No. 12)

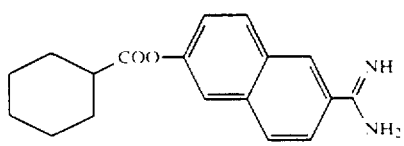

To a solution of 5.0 g of 6-amidino-2-naphthol methanesulfonate in 50 ml of anhydrous pyridine, while being cooled in ice and stirred, was added dropwise 2.6 g of cyclohexanecarbonyl chloride. After stirring for 4.5 hours at room temperature, the reaction mixture was filtered to separate the insolubles which were washed with a small volume of pyridine. The filtrate and washings were added to stirred ethyl ether. The precipitated crystals were collected by filtration, washed with ethyl ether, dissolved in an aqueous methanol solution, and the solution was added to stirred saturated aqueous sodium bicarbonate solution. The precipitated crystals were collected by filtration, washed with water, then with acetone, and dried to yield 2.8 g of the carbonate of the captioned compound. To a suspension of the salt in 20 ml of methanol, while being cooled in ice, was added 1.3 equivalents of methanesulfonic acid followed by ethyl ether to obtain white crystals which were recrystallized from ethanol, yielding 2.0 g of colorless flaky crystals.

Melting point: 261°–265° C.

IR $\nu_{max}^{KBr}$ cm$^{-1}$: 3300, 3100, 2900, 1745, 1670.

NMR (DMSO-d$_6$) δ: 1.00–2.37 (10H, br), 2.40–2.93 (1H, br), 2.50 (3H, s), 7.30–8.67 (6H, m), 9.00–9.67 (4H, br).

EXAMPLE 13

Synthesis of 6-amidino-2-naphthyl 2-cyclopenteneacetate (Compound No. 13):

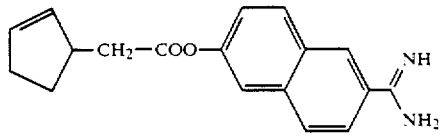

To a solution of 2.2 g of 2-cyclopentene-1-acetic acid in 50 ml of anhydrous pyridine, while being cooled in ice and stirred, was added 4.4 g of DCC. After 30 minutes, 5.0 g of 6-amidino-2-naphthol methanesulfonate was added to the mixture and stirred for 24 hours at room temperature. The precipitate formed by the addition of ethyl ether was collected by filtration, admixed with dimethylformamide, and filtered to remove the insolubles. Ethyl ether was added to the filtrate and the precipitate which was formed was collected by filtration and recrystallized from a dimethyl formamide-ethyl ether mixture to yield 2.1 g of a white powder of 6-amidino-2-naphthyl 2-cyclopenteneacetate methanesulfonate.

Melting point: 199°–201° C.

IR $\nu_{max}^{KBr}$ cm$^{-1}$: 3400–3000, 1750, 1675, 1210, 1175, 1130, 1105, 1045, 775, 545, 520.

NMR (DMSO-d$_6$) δ: 1.17–3.55 (10H, m), 2.50 (3H, s), 5.85 (2H, s), 7.33–8.82 (6H, m), 9.13–9.72 (4H, br).

EXAMPLE 14

Synthesis of 6-amidino-2-naphthyl cyclohexylacetate (Compound No. 14)

To a solution of 2.5 g of cyclohexylacetic acid in 50 ml of anhydrous pyridine, while being cooled in ice and stirred, was added 4.4 g of DCC. After 30 minutes, 5.0 g of 6-amidino-2-naphthol methanesulfonate was added to the mixture, and stirred for 24 hours at room temperature. The insolubles were removed by filtration and ethyl ether was added to the filtrate. The precipitate was collected by filtration and recrystallized from a dimethylformaldehyde-ether mixture to obtain 3.0 g of a white powder of 6-amidino-2-naphthyl cyclohexylacetate methanesulfonate.

Melting point: 203°–205° C.

IR $\nu_{max}^{KBr}$ cm$^{-1}$: 3300, 3150, 2950, 1750, 1680, 1210, 1185, 1050, 780, 550, 525.

NMR (DMSO-d$_6$) δ: 0.88–2.22 (11H, m), 2.53 (3H, s), 2.32–2.92 (2H, m), 7.28–8.92 (6H, m), 9.10–9.92 (4H, br).

EXAMPLE 15

Synthesis of 6-amidino-2-naphthyl 4-cyclohexylbutyrate (Compound No. 15)

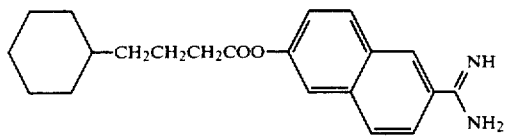

To a solution of 3.0 g of 4-cyclohexylbutyric acid in 50 ml of anhydrous pyridine, while being cooled in ice and stirred, was added 4.4 g of DCC. After 30 minutes, 5.0 g of 6-amidino-2-naphthol methanesulfonate was added to the mixture, and the mixture was stirred for 24 hours at room temeprature. The precipitate which was formed upon addition of ethyl ether was collected by filtration, admixed with dimethylformamide. Ethyl ether was added to the filtrate, and the precipitate was collected by filtration. On recrystallization from a dimethylformamide ethyl ether mixture there were obtained 3.2 g of a white powder of 6-amidino-2-naphthyl 4-cyclohexylbutyrate methanesulfonate.

Melting point: 189°–193° C.

IR $\nu_{max}^{KBr}$ cm$^{-1}$: 3350, 3100, 2900, 2800, 1740, 1670, 1225, 1200, 680, 550, 530.

NMR (DMSO-d$_6$) δ: 0.61–2.10(15H, m), 2.50 (3H, s), 2.37–2.70 (3H, m), 7.30–8.73 (6H, m), 9.13–9.82 (4H, br).

EXAMPLE 16

Synthesis of 6-amidino-2-naphthyl ε-benzyloxycarbonylaminocaproate (Compound No. 16):

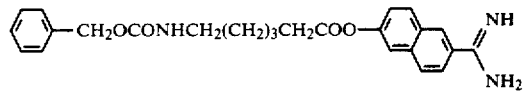

To a solution of 4.7 g of ε-benzyloxycarbonylaminocaproic acid in 50 ml of anhydrous pyridine, while being cooled in ice, was added 4.4 g of DCC. After stirring for 30 minutes, 5.0 g of 6-amidino-2-naphthol methanesulfonate was added to the mixture and stirred overnight at room temperature. The precipitate was separated by filtration and washed with a small volume of pyridine. The filtrate and the washings were added to stirred ethyl ether. The precipitated crystals were collected by filtration, recrystallized from an ethanol-ether mixture, and washed with acetone to obtain 6.2 g of white crystals of 6-amidino-2-naphthyl ε-benzyloxycarbonylaminocaproate methanesulfonate.

Melting point: 119°–122° C.

IR $\nu_{max}^{KBr}$ cm$^{-1}$: 3300, 3100, 1750, 1700, 1675.

NMR (DMSO-d$_6$) δ: 1.18–1.98 (6H, br), 2.38–3.28 (4H, br), 2.48 (3H, s), 5.05 (2H, s), 7.08–8.68 (7H, m), 7.35 (5H, s), 8.77–9.68 (4H, br).

EXAMPLE 17

Synthesis of 6-amidino-2-naphthyl ε-aminocaproate (Compound No. 17)

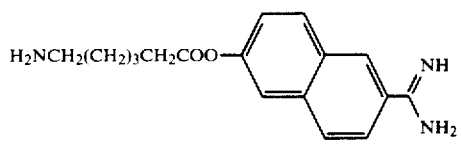

To 40 ml of anhydrous dimethylformamide, were added 4.2 g of 6-amidino-2-naphthyl ε-benzyloxycarbonylaminocaproate methanesulfonate, 1.0 g of methanesulfonic acid, and 0.2 g of 10% palladium-carbon. Hydrogen was passed for 4 hours through the vigorously stirred mixture. After removing the palladium-carbon by filtration, the filtrate was poured into stirred ethyl ether. An oily substance which separated out was washed with ethyl ether and recrystallized from ethanol to obtain 0.87 g of white crystals of 6-amidino-2-naphthyl ε-aminocaproate dimethanesulfonate.

Melting point: 122°–123° C.

IR $\nu_{max}^{KBr}$ cm$^{-1}$: 3300, 3050, 1745, 1665.

NMR (DMSO-d$_6$) δ: 1.33–2.00 (6H, br), 2.37–3.20 (4H, br), 2.48 (6H, s), 7.33–8.67 (9H, m), 9.17–9.63 (4H, br).

EXAMPLE 18

Synthesis of 6-amidino-2-naphthyl ε-guanidinocaproate (Compound No. 18)

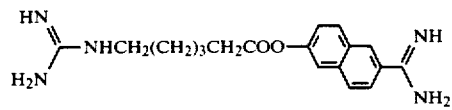

To a solution of 3.7 g of ε-guanidinocaproic acid hydrochloride in 50 ml of pyridine, was added 4.4 g of DCC while cooling in ice. After 30 minutes of stirring, 5.0 g of 6-amidino-2-naphthol methanesulfonate was added and the mixture was stirred overnight at room temperature. The precipitate was collected by filtration, washed with a small volume of pyridine, then with ethyl ether, dissolved in water, and filtered to remove the insolubles. The filtrate was poured into stirred saturated aqueous sodium bicarbonate solution. The precipitated crystals were collected by filtration, washed with water, then with acetone, and dried to obtain the carbonate of the captioned compound. To a suspension of the salt in ethanol, while cooling in ice, was added 2.4 equivalents of methanesulfonic acid followed by ethyl ether to allow an oily substance to separate out. The oily substance was washed with ethyl ether, and recrystallized from ethanol to yield 1.0 g of white granular crystals of 6-amidino-2-naphthyl ε-guanidinocaproate dimethansulfonate.

Melting point: ca. 136° C.

IR $\nu_{max}^{KBr}$ cm$^{-1}$: 3300, 3150, 1740, 1650.

NMR (DMSO-d$_6$) δ: 1.53 (6H, br), 2.74 (6H, s), 2.68 (2H, br), 3.17 (2H, br), 7.00–8.67 (11H, m), 9.10–9.60 (4H, br).

EXAMPLE 19

Synthesis of 6-amidino-2-naphtyl trans-4-benzyloxycarbonylaminomethylcyclohexanecarboxylate (compound No. 19)

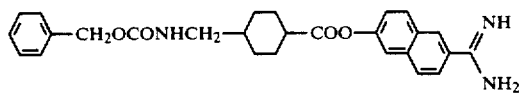

To a solution of 5.0 g of 6-amidino-2-naphthol methanesulfonate in 50 ml of anhydrous pyridine, while being cooled in ice and stirred, was added portionwise 5.5 g of trans-4-benzyloxycarbonylaminomethylcyclohexanecarbonyl chloride. After stirring overnight at room temperature, the insolubles were separated by filtration, and washed with a small volume of pyridine. The filtrate and the washings were poured into stirred ethyl ether. The precipitated crystals were collected by filtration, washed with ethyl ether, dissolved in water and poured into stirred saturated aqueous sodium bicarbonate solution. The precipitated crystals were collected by filtration, washed with water, then with acetone, and dried to obtain the carbonate of the captioned compound. To a suspension of the salt in methanol, while being cooled in ice, was added 1.2 equivalents of methanesulfonic acid followed by ethyl ether to yield 2.2 g of a white powder of 6-amidino-2-naphthyl trans-4-benzyloxycarbonylaminomethylcyclohexanecarbonate methanesufonate.

Melting point: 167°–170° C.
IR $\nu_{max}^{KBr}$ cm$^{-1}$: 3330, 3100, 2900, 1735, 1670.
NMR (DMSO-d$_6$) δ: 0.72–2.35 (10H, br), 2.42 (3H, s), 3.78–4.08 (2H, br), 5.07 (2H, s), 7.15–8.57 (7H, m), 7.38 (5H, s), 9.08–9.50 (4H, br).

EXAMPLE 20

Synthesis of 6-amidino-2-naphthyl trans-4-aminomethylcyclohexanecarboxylate (Compound No. 20).

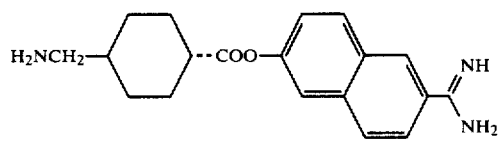

To 13 ml of anhydrous dimethylformamide, were added 0.75 g of 6-amidino-2-naphthyl trans-4-benzyloxycarbonylaminomethylcyclohexanecarboxylate methanesulfonate, 0.2 g of methanesulfonic acid, and 0.1 g of 10% palladium-carbon. Hydrogen was passed for 2 hours through the vigorously stirred mixture at room temperature. After removal of the palladium-carbon by filtration, the filtrate was admixed with ethyl ether. An oily substance which separated out was wahsed with ethyl ether, and recrystallized from ethanol to obtain 0.47 g of white granular crystals of 6-amidino-2-naphthyl trans-p-aminomethylcyclohexanecarboxylate dimethanesulfonate.

Melting point: ca. 147° C.
IR $\nu_{max}^{KBr}$ cm$^{-1}$: 3375, 3060, 1735, 1665.
NMR (DMSO-d$_6$) δ: 1.07–3.00 (12H, br), 2.43 (6H, s), 7.33–8.63 (9H, m), 9.13–9.57 (4H, br).

What is claimed is:

1. An amidine derivative and a pharmaceutically acceptable acid addition salt thereof, said amidine derivative being represented by the formula (I)

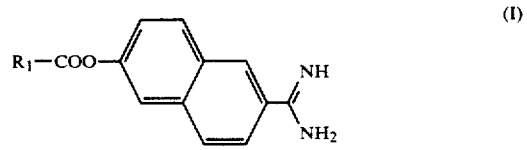

wherein R$_1$ represents a straight-chain or branched-chain alkyl group of 1 to 17 carbon atoms, a straight-chain or branched-chain alkenyl group of 2 to 6 carbon atoms having 1 to 3 double bonds, R$_2$—(CH$_2$)$_n$—, R$_3$—(CH$_2$)$_m$—, or

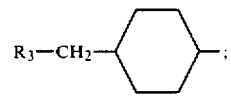

R$_2$ represents a cycloalkyl group of 3 to 6 carbon atoms or a cycloalkenyl group of 3 to 6 carbon atoms having 1 or 2 double bonds; n is 0, 1, 2 or 3; R$_3$ represents an amino or guanidino group or a protected amino or guanidino group; and m is an integer of 1 to 5.

2. An anti-complement agent comprising as an active ingredient an effective anti-complement amount of an amidine derivative represented by the formula (I) or a pharmaceutically acceptable acid addition salt thereof:

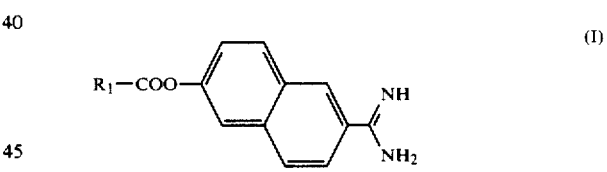

wherein R$_1$ represents a straight-chain or branched-chain alkyl group of 1 to 17 carbon atoms, a straight-chain or branched-chain alkenyl group of 2 to 6 carbon atoms having 1 to 3 double bonds, R$_2$—(CH$_2$)$_n$—, R$_3$—(CH$_2$)$_m$—, or

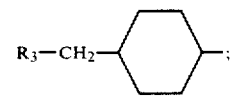

R$_2$ represents a cycloalkyl group of 3 to 6 carbon atoms or a cycloalkenyl group of 3 to 6 carbon atoms having 1 or 2 double bonds; n is 0, 1, 2 or 3; R$_3$ represents an amino or guanidino group or a protected amino or guanidino group; and m is an integer of 1 to 5;
and a pharmaceutically acceptable carrier therefor.

* * * * *